(12) United States Patent
Hoyeyda et al.

(10) Patent No.: US 6,693,168 B1
(45) Date of Patent: Feb. 17, 2004

(54) CHIRAL CYANOAMINES AND METHODS OF PREPARATION

(75) Inventors: Amir Hoyeyda, Belmont, MA (US); Marc L. Snapper, Ashland, MA (US); Kevin Kuntz, Brighton, MA (US); Clinton A. Krueger, Quincy, MA (US); Carolyn Dzierba, Brighton, MA (US)

(73) Assignee: The Trustees of Boston College, Chestnut Hill, MA (US)

( * ) Notice: Subject to any disclaimer, the term of this patent is extended or adjusted under 35 U.S.C. 154(b) by 0 days.

(21) Appl. No.: 09/396,132

(22) Filed: Sep. 14, 1999

Related U.S. Application Data

(60) Provisional application No. 60/100,294, filed on Sep. 14, 1998.

(51) Int. Cl.$^7$ .......................... C07K 7/00; A61K 38/00; G01N 33/53; G01N 33/566; B01J 37/36
(52) U.S. Cl. ................ 530/331; 435/7.1; 435/DIG. 30; 435/DIG. 46; 436/501; 530/333; 530/334; 502/7; 502/150
(58) Field of Search ................................. 530/331, 333, 530/334; 435/7.1, DIG. 46, DIG. 30; 436/501; 502/7, 150

(56) References Cited

U.S. PATENT DOCUMENTS 5,939,268 A * 8/1999 Boger ........................ 435/7.1

OTHER PUBLICATIONS

Thompson et al, Chem. Rev. vol. 96 (1), pp. 555–600, 1996.*

Schier et al. Aust. J. Chem. 1974, Vol 27, No 11, pp. 2455–2462.*

K.D. Cole et al., "Discovery of Chiral Catalysts Through Ligand Diversity; Ti–Catalyzed Enantioselective Addition of TMSCN to Meso Epoxides", *Angewandte Chemie, International Edition*, vol. 35, No. 15, pp. 1668–1671, 1996.

E.J. Corey et al., "Eantioselective Synthesis of α–Amino Nitriles from N–Benzhydryl Imines and HCN with a Chiral Bicyclic Guanidine as Catalyst", *Organic Letters*, vol. 1, No. 1, pp. 157–160, 1959.

Haruro Ishitani et al., "Catalytic Enantioselective Synthesis of α–Aminonitriles with a Novel Zirconium Catalyst", *Angew. Chem. Int. Ed.*, vol. 37, No. 22, pp. 3186–3188, 1998.

Mani S. Iyer et al., "Asymmetric Catalysis of the Strecker Amino Acid Synthesis by a Cyclic Dipeptide", *J. Am. Chem. Soc.*, vol. 118, pp. 4910–4911, 1996.

K. Jayasimhulu et al., "Nitrile Elimination and Hydrogen Rearrangement Upon Electron Impact Upon Schiff base Peptide Esters" XP002131542 *Org. Mass Spectrom*, vol. 13, No. 9, pp. 540–543, 1978. *Chemical Abstracts*, vol. 91, No. 3, abstract No. 21044, 1979.

Clinton A. Krueger et al., "Ti–Catalyzed Enantioselective Addition of Cyanide to Imines. A Practical Synthesis of Optically Pure α–Amino Acids", *J. Am. Chem. Soc.*, vol. 121, 4284–4285, 1999.

K.D. Shimizu et al., "Search for Chiral Catalysts through Ligand Diversity; Substrate–Specific Catalysts and Ligand Screening on Solid Phase", Angewandte Chemie. International Edition, vol. 36, No. 16, pp. 1704–1707, 1997.

Matthew S. Sigman et al., "Schiff Base Catalysts for the Asymmetric Strecker Reactino Identified and Optimized from Parallel Synthesis Libraries", *J. Am. Chem.. Soc.*, vol. 120, pp. 4901–4902, 1998.

Matthew S. Sigman et al., "Enaritioselective Addition of Hydrogen Cyanide to Immines Catalyzed by a Chiral (Salen) A1 (III) Complex", *J. Am. Chem. Soc.*, vol. 120, 5315–5316, 1998.

PCT Search Report issued Mar. 27, 2000 in connection with corresponding PCT Application PCT/US 99/21020.

PCT Written Opinion issued May 31, 2000 in connection with corresponding PCT Application PCT/US 99 21020.

* cited by examiner

*Primary Examiner*—Maurie Garcia Baker
(74) *Attorney, Agent, or Firm*—Fish & Richardson PC

(57) ABSTRACT

Methods for preparing chiral non-racemic cyanoamines are provided. The methods are useful, e.g., for preparing chiral amino acids.

5 Claims, No Drawings

CHIRAL CYANOAMINES AND METHODS OF PREPARATION

CROSS REFERENCE TO RELATED APPLICATION

This application claims priority from U.S. Provisional Application Serial No. 60/100,294, filed on Sep. 14, 1998, which is incorporated herein by reference in its entirety.

FIELD OF THE INVENTION

The invention relates to chiral cyanoamines and methods of preparation.

BACKGROUND OF THE INVENTION

Recent research in the area of chiral catalysis has illustrated the ability to transform prochiral, inexpensive materials into optically pure, valuable chemicals. Chiral amino acids, amino alcohols, and diamines have been used in the synthesis of pharmaceuticals, diagnostics, and materials. With the exception of natural amino acids, which may be isolated from fermentation or hydrolysis of proteins, these materials are often time consuming and costly to manufacture.

One previously known route to prepare amino acids is the Strecker synthesis, a modified Mannich reaction in which a carbonyl-containing compound (either a ketone or aldehyde) is condensed with ammonia (or another amine) to form an imine component, which subsequently reacts with sodium cyanide to form a cyanoamine, which can then be hydrolyzed to yield an amino acid. This method works for aliphatic and aromatic carbonyl components. However, this method provides only racemic products in the absence of a chiral reagent. While chiral amino acids have been made using the Strecker methodology, these methods have generally depended upon the use of a chiral amine to form the imine component. The necessity of using a chiral reagent in stoichiometric quantity often makes such methods quite expensive.

SUMMARY OF THE INVENTION

The present invention relates to chiral catalysts that can be used to transform chemically compatible imines to optically enriched cyanoamines, to the application of such catalysts to the synthesis of optically enriched cyanoamines, and to the preparation of optically enriched amino acids, optically enriched amino alcohols, or optically enriched diamines.

In general, catalysts useful in the methods of the invention have the structure (Formula I):

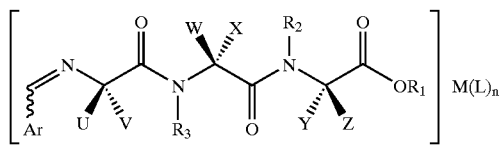

where U, V, W, X, Y, and Z can each be, independently, hydrogen, a substituted or unsubstituted alkyl group (which can be straight- or branched chain, or may be cyclic), an aryl group (including heteroaryl), an aralkyl group, an alkaryl group, or a heterocyclic group; Ar is a substituted or unsubstituted aryl group or hydroxyalkyl group; $R_1$ is an alkyl group (e.g., lower alkyl), an aryl group, or a heterocyclic group; $R_2$ and $R_3$ are each, independently, hydrogen, an alkyl group (e.g., lower alkyl, an aryl group, or a heterocyclic group; M is a metal ion (including a proton, a main group metal ion, or a transition metal ion); L is a counterion; and n is an integer, e.g., an integer from 1 to 3. In certain embodiments, Y and Z are both hydrogen. In other embodiments, one, some, or all of U, V, W, X, Y, and Z are independently selected from side chain moieties of naturally occurring or synthetic amino acids.

Catalysts of the invention can be prepared by combining one equivalent of a metal ion with a ligand of Formula I, such that a catalyst complex is formed.

In one aspect, the invention provides catalysts for the asymmetric synthesis of amino acids using tripeptide-based complexes.

The invention also features methods for determining the optimal catalyst for the transformation of an imine described by the structure (1) of Scheme 2 (infra) to an optically enriched cyanoamine when that structure is described by the complex formed between $M(L)_n$ and the ligand.

In addition, the invention features a synthetic route to both enantiomers of tert-leucine in an optically enriched form, and a synthetic route to either enantiomer of any unnatural amino acid in an optically enriched form.

The invention also provides a synthetic route to all diastereomers of an amino acid with a chiral side chain in optically enriched form.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The present invention relates to catalysts useful for promoting the formation of chiral, non-racemic cyanoamines, to combinatorial libraries (arrays) of such catalysts, to the use of an array of catalysts for selecting catalysts for the synthesis of chiral materials, and to the use of such catalysts for preparation of optically enriched materials.

A catalyst is a material that facilitates a desired outcome for a specific reaction and is not consumed (or is regenerated) in the course of the reaction by mechanistic pathways. The term "catalyst" may be applied to a metal, a ligand-metal complex, or to a ligand alone that performs the desired transformation.

Reactants or materials that are termed "chemically compatible" are those reactants or materials that do not undesirably impede or prevent a desired reaction from occurring, e.g., by destroying or interfering with the catalyst, ligand, metal or any other component of the reaction. Thus, reactants or materials that would cause an undesired outcome or prevent the desired transformation from occurring are incompatible and are not preferred for use in the methods described herein.

As will be appreciated by the skilled artisan, "chirality" refers to the innate handedness of a molecule. A chiral material is "optically enriched", when the material is present in non-racemic form, i.e., when an excess of one enantiomer is present over the complimentary (antipodal) enantiomer. Optical enrichment is commonly expressed as enantiomeric excess, i.e., the excess of one enantiomer over its antipode. An enantiomeric excess of 100% indicates optical purity, i.e., the absence of one enantiomer. In preferred embodiments, reactions according to the invention can provide optically enriched, and preferably substantially optically pure products. In certain embodiments, the methods of the invention can provide a desired product (e.g., a cyanoamine) in at least 50% enantiomeric excess, more preferably at least about 60%, 70%, 80%, 90%, 95%, or 99% enantiomeric excess.

"Prochiral" refers to planar or achiral material that can react in a chiral environment to provide a chiral product.

The term "metal," as used herein, includes a proton, a main-group metal atom or ion, a transition metal atom or ion, or any other metal atom or ion that can be used to form an active catalyst according to the invention. Metals present as components of catalysts of the invention are generally present in ionic, rather than elemental, forms (e.g., titanium in the +4 oxidation state). Exemplary metals include titanium, zirconium, vanadium, chromium, cobalt, nickel, copper, zinc, and manganese. The term "counterion" refers to any chemically compatible species used for charge balance. Exemplary counterions include halide (e.g., chloride, fluoride, bromide, or iodide), hydroxide, halite, alkoxide, boron halide, sulfate, phosphate, or other salt-forming anions.

A "library" is a collection of compounds (e.g., as a mixture or as individual compounds) synthesized from various combinations of one or more starting components (e.g., a combinatorial library). At least some of the compounds must differ from at least some of the other compounds in the library. A library can, for example, include 5 to 10, 50, 100, 1,000, 10,000, 50,000, or even 100,000 or more different compounds (i.e., not simply multiple copies of the same compounds, although some compounds in the library may be duplicated or represented more than once). Each of the different compounds, whether they have a different basic structure or different substituents, will be present in an amount such that its presence can be determined by some means, e.g., can be isolated, analyzed, and detected with a receptor or suitable probe. The actual quantity of each different compound needed so that its presence can be determined will vary due to the actual procedures used and may change as the technologies for isolation, detection, and analysis advance. When the compounds are present in a mixture in substantially equimolar amounts, for example, an amount of 100 picomoles of each compound can often be detected.

Libraries can include both libraries of individual compounds (e.g., present substantially as a single compound-per-well, e.g., made via parallel synthesis) and mixtures containing substantially equimolar amounts of each desired compound (i.e., wherein no single compound dominates or is completely suppressed in any assay). Either library format can allow identification of an active compound discovered in an assay; spatially arranged (or spatially addressable) array formats (see, e.g., U.S. Ser. No. 09/061,572, filed Apr. 16, 1998, and U.S. Pat. No. 5,712,171) can also be used to develop structure-activity relationships (SARs).

The terms "array" or "set" refer to structurally related groups or libraries of compounds, ligands, metal-ligand complexes, or metals that are organized in a spatially addressable format or in a one-dimensional line such that analysis of reagents, reactions, substrates, or products provides data from which to select an optimal compound.

The catalysts of the present invention have a formula which may be schematically represented by the following structure:

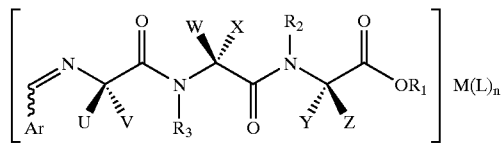

wherein U, V, W, X, Y, and Z are each, independently, hydrogen, substituted or unsubstituted alkyl (which can be straight- or branched chain, or may be cyclic), aryl (including heteroaryl), aralkyl, alkaryl, heterocyclic, or the like; Ar is a substituted or unsubstituted aryl group or hydroxyalkyl group (e.g., a 2-hydroxyphenyl or 2-hydroxyalkyl group); $R_1$ is alkyl (e.g., a lower alkyl, such as methyl), aryl, or heterocyclyl; $R_2$ and $R_3$ are each independently selected from the group consisting of hydrogen, alkyl (e.g., lower alkyl), aryl, and heterocyclyl groups; M is a metal ion (e.g. a proton, a main group metal ion, or a transition metal ion); L is a counterion; and n is an integer, e.g., an integer from 1 to 3. In certain embodiments, Y and Z are both hydrogen. Any of U, V, W, X, Y, and Z can optionally be joined to form a cyclic moiety, and any of Ar, U, V, X, Y, Z, $R_1$, $R_2$, and $R_3$ can optionally be immobilized to a solid or insoluble support. In certain embodiments, one, some, or all of U, V, W, X, Y, and Z are independently selected from side chain moieties of naturally occurring or synthetic amino acids. It will be appreciated that U, V, W, X, Y, and Z are preferably selected to be chemically compatible with the desired reaction. For example, hydroxyl groups, or strongly charged groups such as guanidinyl groups, could, in certain instances, interfere with the desired reactions. However, as described in the Examples below, such groups may be masked to prevent such interference. For example, as shown in Example 1, ligands were prepared using tosyl-protected arginine to minimize interference from the basic guanidinyl moiety of the arginine side chain.

The functional groups U, V, W, X, Y, Z, $R_1$, $R_2$, $R_3$ and Ar of the imino ligand (i.e, the portion of the catalyst surrounded by brackets in Formula I) can be varied according to the substrate of the imine substrate to be converted to a cyanoamine, and the structure and stereochemistry of the desired product.

The catalysts of the invention can be prepared by combining a metal salt with a peptidic (e.g., tripeptidic) ligand. The synthesis and design of peptides is well known in the art and is detailed in the literature of the art. Various reagents, starting materials, and functional groups provide numerous routes to the tripeptide ligand precursors described herein here. These routes can involve more or less expensive reagents, naturally occurring or synthetic building blocks, low and high-yielding reactions, and extensive or minimal preparatory procedures and purifications. The catalysts of the invention are reusable and are generally required in relatively small quantities. Thus, the tripeptide ligand precursors and derived catalysts described herein are not limited by the synthetic complexity and expense of material, and any known synthetic strategy can be used to make them.

For example, the following synthetic route (Scheme 1) can be used.

Scheme 1

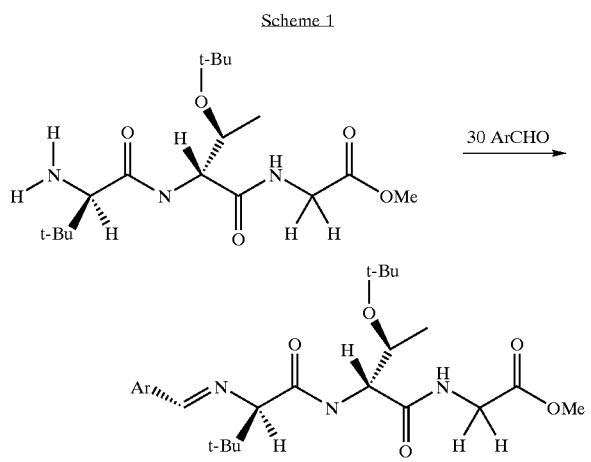

Scheme 2

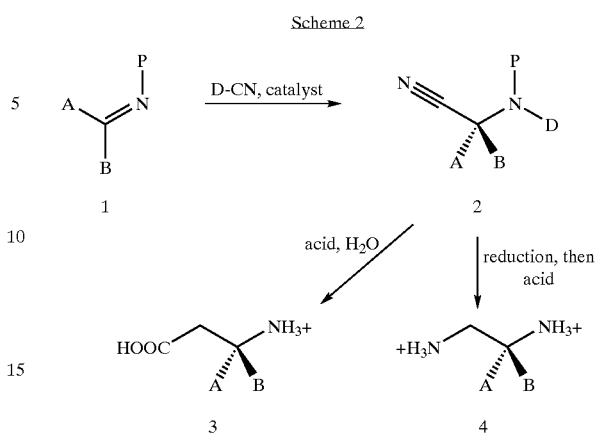

A tripeptide moiety (e.g., a tripeptide methyl ester) can be converted to an imino ligand useful in a catalyst of the invention by standard methods. For example, the imino ligand can be prepared via a one-pot azeotropic reaction of the tripeptide ligand precursor and an aldehyde by known methods (e.g., Schiff base formation). The resulting Schiff bases are generally stable compounds and can be made in quantity for scale-up or can be constructed in parallel for large-scale array preparation in great numbers.

In certain embodiments, the catalysts of the invention can be prepared in isolated, purified form, i.e., substantially free (i.e., at least 90% pure) of other reaction components such as the reaction substrate or products. Catalysts can also be of 98%, 99%, or greater purity. For example, catalysts can be prepared in a solution, e.g., as described in Example 1, infra, from which the solvent can be removed to provide the isolated catalyst. In certain embodiments, the catalysts can be prepared immobilized on a solid or insoluble support, such as resin beads, and the beads can be filtered to remove any solvent, thereby preparing an isolated, purified catalyst on a solid support.

The transformation of an imine to a cyanoamine according to the invention is schematically depicted in Scheme 2, in which a protected imine 1 (which can be prepared, e.g., by reaction of a protected amine with an aldehyde or ketone) is transformed into a protected cyanoamine 2 by reaction with cyanide donor D-CN in the presence of a catalyst of Formula I. In Scheme 2, the groups A and B can be, e.g., hydrogen, alkyl, aryl, heterocyclyl, and the like; preferably, A and B are not the same, so that the imine 1 is prochiral. The nitrogen of compounds 1 and 2 is shown as protected by a group P which can be a hydrogen atom, or a protecting group as described in more detail below. The protected cyanoamine can then by hydrolyzed and deprotected to afford an amino acid 3, e.g., by treatment with acid, or the cyano functionality can be reduced to an amine and the molecule deprotected to form a diamine 4 (shown as the diacid).

The protecting group P can generally be chosen for two properties: first, to provide optimal selectivity of cyanide addition to the imine 1 to provide one chiral product of cyanide addition in preference to the antipode; and second, for facile removal of the protecting group upon completion of the reaction, to yield a desired product. The protecting group can be any group known for protection of amines which is stable to the reaction conditions (see, e.g., Greene and Wuts, "Protective Groups in Organic Synthesis", John Wiley & Sons, 1991). Preferred protecting groups include diphenylmethyl and alkoxybenzylamines and bis(alkoxybenzyl)amines if A and B are not aromatic, and bis(alkoxybenzyl)amines if one of A and B is aromatic. In the former case, hydrogenolysis or acid cleavage are used according to the more favorable synthetic outcome. Ultimate selection of P can be effected by testing imines that include variants of compatible groups P and subjecting them to reaction as described herein.

The cyanide donor D-CN can be hydrocyanic acid (HCN, e.g., as a liquid or in solution), a salt such as sodium or potassium cyanide, or a non-ionic donor such as trimethylsilylcyanide (TMS-CN), available, e.g., from Aldrich Chemical Co., Milwaukee, Wis.). Other cyanide donors, such as t-butyldiphenylsilyl cyanide (TBDPS-CN) and t-butyldimethylsilyl cyanide (TBS-CN) (Aldrich), can also be used. It will be appreciated that use of a labile cyanide donor such as TMS-CN may require the use of non-aqueous, non-alcoholic reaction solvents and/or anhydrous reaction conditions. It will also be appreciated that the use of a reagent such as TMS-CN can result in (temporary) protection of the amine group of the product cyanoamine (e.g., the amine of cyanoamine 2 in Scheme 2 would be protected with a trimethylsilyl group, which could be readily removed by acid treatment). In certain embodiments, the cyanide donor can be selected to provide an advantageous protection of the nitrogen atom in the cyanoamine. For example, the TBDPS group is generally more stable than the TMS group in protecting a nitrogen atom. Thus, if more robust protection of the amine is desired, TBDPS-CN would generally be preferred to TMS-CN.

The invention provides combinatorial arrays or libraries of imino ligands and catalysts. Such combinatorial libraries can be prepared according to a variety of methods. For example, a plurality of tripeptides (of a number Q) can be synthesized by known methods and reacted with aldehydes (of a number R) to form the corresponding schiff bases (imino ligands). These imino ligands (quantity Q×R) can then be treated with equimolar amounts of metal salts (of a number S), varying not only the metal, but the counterion as well, to form an array or library of (Q×R×S=T) metal-ligand complexes. This entire library of catalysts, or portions thereof, can be applied to the selected imine substrate to provide the optimum substrate and catalyst in this compound class. A library of the invention can include, e.g., 10, 20, 50, 100, 500, 1000, 5000, 10000, 15000, 20000, or more different imino ligands or catalysts.

The invention also provides methods for selecting an optimal catalyst for catalyzing a particular transformation. For example, a catalyst library of the invention can be screened using a selected imine compound as a reaction substrate, and the results of reaction with some or all of the catalysts can then be analyzed. Such a library of catalysts can be produced, e.g., as described herein. A catalyst can be selected based upon such considerations as product yield, product optical purity, freedom from impurities, and the like.

An alternate method to determine the optimum catalyst uses the positional scanning of P, Ar, U, V, W, X, Y, and Z, by varying a singular component exhaustively along one axis, while holding all other variables constant, preferably in a logically ordered array format. For a discussion of logically ordered, spatially arranged arrays, see, e.g., U.S. Pat. No. 5,712,171. For example, a series of 30 Schiff base derivatives is defined by reacting thirty different aldehydes with the same tripeptide.

In certain embodiments, these steps can be iteratively optimized to provide the best catalyst for each specific application.

Given the set of potential catalysts available from the corresponding ligand-metal complexes, and the variety of α-cyanoamines that can be prepared from imine substrates, a wide variety of materials can be made using the methods of the invention. For example, as shown in Scheme 2, acid hydrolysis of the cyanoamine can be used according to well known methods to obtain an amino acid, which in turn can be reduced using lithium aluminum hydride (LAH) to form valuable amino alcohols. Direct reduction of the cyanoamine with a reducing agent such as LAH, followed by appropriate removal of the protective group P, provides the corresponding chiral diamine (e.g., compound 4 in Scheme 2).

The side chain groups A and B of the imine substrate 1 (Scheme 2) can be the same or different, can have a variety of structures, and can differ markedly from one another in their physical or structural properties. The side groups A and B can be hydrogen; substituted or unsubstituted alkyl (including branched and straight chain), substituted or unsubstituted aryl, aralkyl, alkaryl, carbocyclic, heterocyclic groups, or other moieties such as functional side chains of natural and unnatural amino acids, nucleosides, carbohydrates, structures which possess known pharmacological activity including, but not limited to, benzodiazepines, piperazines, dibenzazepines, prostaglandins, 1-(3-alkoxy-2-hydroxy)propanes, piperidines, 4-aryl-4-hydroxypiperidines, pyrazoles, 1-(2-hydroxy-2-aryl)ethanes, tropanes, or macrolides. However, the groups A and B of the substrate are preferably selected to be compatible with the desired transformation.

A "linear or branched chain alkyl group" is any substituted or unsubstituted acyclic carbon-containing compound, including alkanes, alkenes, or alkynes. Alkyl groups having up to 30 carbons are preferred. "Lower alkyl" refers to an alkyl group having from 1 to 8 carbon atoms in a straight or branched chain. Unless otherwise stated, lower alkyl groups are preferred. Examples of alkyl groups include lower alkyl, for example, methyl, ethyl, n-propyl, 2-propyl, n-butyl, sec-butyl, isobutyl, tert-butyl; higher alkyl, for example, nonyl, decyl, 5-ethyl-3-methyldecyl, or the like; lower alkene, for example, ethylene, 2-propylene, 1-propylene, 3-propylene, butylene, 2-methylpropylene, or butadienyl; higher alkene, for example, 1-decene, 3-nonene, 2,6-dimethyl-5-octenyl, or 6-ethyl-5-octenyl; alkynyl, for example, 1-ethynyl, 2-butyn-3-yl, or 1-pentyn-3-yl. The ordinary skilled artisan is familiar with the variety, selection, and nomenclature of linear and branched alkyl groups, all of which are within the scope of the present invention.

Additionally, an alkyl group may or may not also contain substituents in which one of the hydrogen groups is replaced by a functional group. Functional groups include, but are not limited to, hydroxyl, amino, carboxyl, carboxamido, amido, alkylamino, arylamino, alkylamino, aralklylamino, carboalkoxy, alkoxy, and halo (fluorine, chlorine, bromine, iodine). Specific substituted functional groups can be, for example, alkoxy, methoxy, ethoxy, 1-propoxy, 2-propoxy, 3-dodecyloxy, and the like, polyhydroxy such as 1-(3-hydroxypentoxy, 1-(2,4,5,6-tetrahydroxycyclohexyloxy, methamino, aminophenyl, aminomethyl, diethylamino, pyrrolidyl, piperidinyl, dibenzylamino, perhydroquinolyl, and the like, nitro, nitroso, azo, formamidino, formamido, acetimido, butanimido, acetanilido, benzamido, methoxycarbonyl, ethoxycarbonyl, benzyloxycarbonyl methoxymethyl ethoxymethyl, 2-ethoxyethyl, and 1-ethoxyethyl. As used herein, substituted and unsubstituted carbocyclic groups of up to about 20 carbon atoms means cyclic carbon-containing compounds, including but not limited to, cyclopentyl, cyclohexyl, cycloheptyl, and adamantyl. Such cyclic groups may also contain various substituents in which one or more hydrogens are replaced by functional groups. Such functional groups can include those described above and lower alkyl groups as described above. Furthermore, one of the carbon atoms and its associated hydrogen atoms contained within the ring can be replaced by an appropriate heteroatom to form a heterocyclic moiety. As specific, non-limiting examples, side group A (of imine substrate 1 of Scheme 2) can be 2-cyclohexanol, or 3-piperidin-4-ol.

As used herein, substituted or unsubstituted aryl groups are hydrocarbons or heterocyclic rings bearing a system of conjugated double bonds, usually comprising (4n+2) pi bond electrons, where n is an integer. Examples of aryl groups include, but are not limited to, phenyl, naphthyl, anisyl, tolyl, and xylenyl. The present invention also includes aryl groups including, but not limited to, aryloxy, aralkyl, aralkyloxy, and heteroaryl groups such as pyridinyl, furyl, thienyl, pyrazinyl, quinolyl, piperazinyl, and oxazolinyl. These aryl groups may be substituted with any number of functional groups as described above. In addition to these functional groups, the side groups can be substituted with any multiple or combination of chemically compatible functional groups well known to any synthetic organic chemist ordinarily skilled in the art.

Additionally, any of the groups U, V, W, X, Y, Z, Ar, $R_1$, $R_2$, or $R_3$ can be attached, either covalently or via strong non-bonded interaction to a solid support or surface, rendering the catalyst or metal-ligand complex heterogeneous in relation to the substrate. The solid support can be any macromolecular support known to a person ordinarily skilled in the art. Such macromolecules or solid supports can include, but are not limited to, porous and non-porous inorganic components such as zirconia, alumina, silica, rutile, titania and the like, as well as porous and non-porous organic media including, but not limited to, styrene beads, styrene-divinylbenzene crosslinked beads, derivatives of polymethacrylate, derivatives of polyacrylamide, PVA beads and the like. The molecular weight of these molecules can range from about 1000 daltons to 10,000, 100,000, 1,000,000 or more daltons. They may be in various forms such as particles (100–5000 angstroms), beads (0.5–1000 microns), membranes, gels, surfaces on macroscopic media, or surfaces of composites or coatings.

The invention also provides methods for the preparation of chiral (non-racemic) cyanoamine compounds. The methods include the step of reacting an imine substrate (e.g., an imine represented by the structure 1 of Scheme 2) with a cyanide donor in the presence of an effective amount of a catalyst of Formula I, under conditions such that a chiral cyanoamine is produced. In general, the catalyst can be present in an amount ranging from about 0.001 mole percent to about 50 mole percent, based on the amount of imine substrate. More preferably, the catalyst is present in an amount from 0.01 to 10%, more preferably 0.1 to 1%, based on starting imine. However, the catalyst could be used in stoichiometric amount, or even in molar excess, if desired.

The methods of the invention can be performed in appropriate reaction solvents, if desired. A solvent, if used, is preferably anhydrous, with aprotic solvents such as benzene and toluene being preferred. Other solvents which can be used include tetrahydrofuran, dichloromethane, and other solvents not incompatible with the reaction conditions. In certain embodiments, the reactions can be performed under an inert atmosphere, such as a blanket of nitrogen or argon.

In certain embodiments, reactions can be carried out on solid or insoluble supports, if desired. For example, an immobilized catalyst can be used to catalyze the transformation of an imine to a cyanoamine. In some instances, the imine can be present in solution, and the catalyst, bound to a solid support, can be added to the solution. The presence of reagents (or, alternatively, substrates) on the solid support can provide certain advantages, such as ease of reaction work-up or product isolation. In addition, the use of a solid-supported catalyst can facilitate recovery and reuse of catalyst, and can thus provide greater economy of materials.

The methods of the invention can be performed at a variety of temperatures, e.g., in the range of about −78° C. to about 100° C., more preferably from about 0° C. to about 80° C. Advantageously, the reactions can occur at about room temperature, thereby minimizing or eliminating any need for heating or cooling of the reaction vessel.

In a preferred embodiment of the invention, one of the groups A or B (of imine 1 from Scheme 2) is a hydrogen atom and the other group is a functional group as described above. Alkyl and aryl groups are preferred. Such imines can be prepared, e.g., by reaction of an amine with an aldehyde. In a preferred embodiment, the protecting group P of the nitrogen is diphenylmethyl, and the cyanide counterpart D is trimethylsilyl.

In one embodiment, the metal salt $M(L)_n$ is titanium tetraisopropoxide. In certain other embodiments, the Ar group (of the ligand) is a hydroxyaryl group, especially a hydroxyphenyl group (preferably a 2-hydroxyphenyl group, e.g., prepared by condensation of a tripeptide with a salicylaldehyde); the groups U and V are a hydrogen atom and a tertiary-butyl group; and the groups W and X are a hydrogen atom and a 1-tertiary-butyloxyl-1-ethyl group; and Y and Z are both hydrogen; $R_1$ is methyl, and $R_2$ and $R_3$ are both hydrogen. The application of these catalysts after the selection process to the substrates provides precursors to either enantiomer of any natural or unnatural amino acid in optically enriched form, depending on the respective orientations of U, V, W, and X.

In certain other embodiments, an alcohol, usually corresponding to the alkoxide of the metal center, is added slowly to facilitate the reaction, decrease catalyst loading, increase catalyst turnover, and increase consumption of starting imine. For example, as described in Example 3, infra, an alcohol such as isopropanol can be added to a reaction in which the metal counterion is isopropoxide (e.g., the metal component is titanium tetraisopropoxide). In certain preferred embodiments, up to one equivalent of an alcohol can be added to the reaction mixture to promote complete reaction.

In a specific embodiment of the invention (referring to Scheme 2), B, U, and X are hydrogen, A and V are tertiary-butyl groups, Ar is 3,5-dichloro-2-hydroxyphenyl, D is trimethylsilyl, P is diphenylmethyl, W is a 1-tertiary-butyloxy-1-ethyl group, Y and Z are hydrogen, $R_1$ is methyl, and $R_2$ and $R_3$ are both hydrogen; and the metal salt $M(L)_n$ is titanium tetraisopropoxide. This reaction affords the S-tertiary-butylcyanoamine to provide the corresponding S-tert-leucine upon hydrolysis in optically enriched form.

In another specific embodiment of the invention, B, V, and W are hydrogen, A and U are tertiary-butyl groups, Ar is 3,5-dichloro-2-hydroxyphenyl, D is trimethylsilyl, P is diphenylmethyl, $R_1$ is methyl, and $R_2$ and $R_3$ are both hydrogen; X is a 1-tertiary-butyloxy-1-ethyl group and the metal salt $M(L)_n$ is titanium tetraisopropoxide. This reaction affords the R-tertiary-butylcyanoamine to provide the corresponding R-tert-leucine upon hydrolysis in optically enriched form.

In another embodiment of the invention, A is phenyl, B, U, and X are hydrogen, V is a tertiary-butyl group, Ar is 2-hydroxy-5-methoxyphenyl, D is trimethylsilyl, P is diphenylmethyl, W is a 1-tertiary-butyloxy-1-ethyl group, R1 is methyl, and R2 and R3 are both hydrogen; and the metal salt M(L)n is titanium tetraisopropoxide. This reaction affords the R-phenylcyanoamine to provide the corresponding R-phenylglycine upon hydrolysis in optically enriched form.

In other embodiments of the invention, A is phenyl, B, V, and W are hydrogen, U is a tertiary-butyl group, Ar is 2-hydroxy-5-methoxyphenyl, D is trimethylsilyl, P is diphenylmethyl, X is a 1-tertiary-butyloxy-1-ethyl group group, $R_1$ is methyl, and $R_2$ and $R_3$ are both hydrogen; and the metal salt $M(L)_n$ is titanium tetraisopropoxide. This reaction affords the S-phenylcyanoamine to provide the corresponding S-phenylglycine upon hydrolysis in optically enriched form.

In yet another embodiment of the invention, A is a 2-chlorophenyl group, B, U, and X are hydrogen, V is a tertiary-butyl group, Ar is 3,5-dichloro-2-hydroxyphenyl, D is trimethylsilyl, P is diphenylmethyl, W is a 1-tertiary-butyloxy-1-ethyl group, $R_1$ is methyl, and $R_2$ and $R_3$ are both hydrogen; and the metal salt $M(L)_n$ is titanium tetraisopropoxide. This reaction affords the S-2-chlorophenylcyanoamine to provide the corresponding S-2-chlorophenylglycine upon hydrolysis in optically enriched form.

In another specific embodiment of the invention, A is a 2-chlorophenyl group, B, V, and W are hydrogen, U is a tertiary-butyl group, Ar is 3,5-dichloro-2-hydroxyphenyl, D is trimethylsilyl, P is diphenylmethyl, X is a 1-tertiary-butyloxy-1-ethyl group, $R_1$ is methyl, and $R_2$ and $R_3$ are both hydrogen; and the metal salt $M(L)_n$ is titanium tetraisopropoxide. This reaction affords the R-2-chlorophenylcyanoamine to provide the corresponding R-2-chlorophenylglycine upon hydrolysis in optically enriched form.

In yet other embodiments, A is a 4-methoxyphenyl group, B, U, and X are hydrogen, V is a tertiary-butyl group, Ar is 3,5-dichloro-2-hydroxyphenyl, D is trimethylsilyl, P is diphenylmethyl, W is a 1-tertiary-butyloxy-1-ethyl group, $R_1$ is methyl, and $R_2$ and $R_3$ are both hydrogen; and the metal salt $M(L)_n$ is titanium tetraisopropoxide. This reaction affords the S-4-methoxyphenylcyanoamine to provide the corresponding S-4-methoxyphenylglycine upon hydrolysis in optically enriched form.

In another specific embodiment of the invention, A is a 4-methoxyphenyl group, B, V, and W are hydrogen, U is a tertiary-butyl group, Ar is 3,5-dichloro-2-hydroxyphenyl, D is trimethylsilyl, P is diphenylmethyl, X is a 1-tertiary-butyloxy-1-ethyl group, $R_1$ is methyl, and $R_2$ and $R_3$ are both hydrogen; and the metal salt $M(L)_n$ is titanium tetraisopropoxide. This reaction affords the R-4-methoxyphenylcyanoamine to provide the corresponding R-4-methoxyphenylglycine upon hydrolysis in optically enriched form.

In other embodiments of the invention, A is a 2-naphthyl group, B, U, and X are hydrogen, V is a tertiary-butyl group, Ar is 5-methoxy-2-hydroxyphenyl, D is trimethylsilyl, P is diphenylmethyl, W is a 1-tertiary-butyloxy-1-ethyl group, $R_1$ is methyl, and $R_2$ and $R_3$ are both hydrogen; and the metal salt $M(L)_n$ is titanium tetraisopropoxide. This reaction affords the S-2-naphthylcyanoamine to provide the corresponding S-2-naphthylglycine upon hydrolysis in optically enriched form.

In yet another embodiment of the invention, A is a 2-naphthyl group, B, V, and W are hydrogen, U is a tertiary-butyl group, Ar is 5-methoxy-2-hydroxyphenyl, D is trimethylsilyl, P is diphenylmethyl, X is a 1-tertiary-butyloxy-1-ethyl group, $R_1$ is methyl, and $R_2$ and $R_3$ are both hydrogen; and the metal salt $M(L)_n$ is titanium tetraisopropoxide. This reaction affords the R-2-naphthylcyanoamine to provide the corresponding R-2-naphthylglycine upon hydrolysis in optically enriched form.

In another specific embodiment of the invention, A is a cyclohexyl group, B, U, and X are hydrogen, V is a tertiary-butyl group, Ar is 2-hydroxyphenyl, D is trimethylsilyl, P is diphenylmethyl, W is a 1-tertiary-butyloxy-1-ethyl group, $R_1$ is methyl, and $R_2$ and $R_3$ are both hydrogen; and the metal salt $M(L)_n$ is titanium tetraisopropoxide. This reaction affords the S-cyclohexylcyanoamine to provide the corresponding S-cyclohexylglycine upon hydrolysis in optically enriched form.

In another embodiment of the invention, A is a cyclohexyl group, B, V, and W are hydrogen, U is a tertiary-butyl group, Ar is 2-hydroxyphenyl, D is trimethylsilyl, P is diphenylmethyl, X is a 1-tertiary-butyloxy-1-ethyl group, $R_1$ is methyl, and $R_2$ and $R_3$ are both hydrogen; and the metal salt $M(L)_n$ is titanium tetraisopropoxide. This reaction affords the R-cyclohexylcyanoamine to provide the corresponding R-cyclohexylglycine upon hydrolysis in optically enriched form.

The components of the ligand and metal can be varied to find an optimal catalyst for conversion of any given imine to an optically enriched cyanoamine. Screening an entire library of these ligand-metal complexes against an imine can allow identification of the optimum catalysts contained within that library. By controlling the chirality of the ligand, the desired cyanoamine enantiomer can be made selectively.

Each functional group of the tripeptidic ligand (e.g., U, V, W, X, Y, Z, Ar, $R_1$, $R_2$, and $R_3$), metal, counterion, and protecting group on the nitrogen of the imine substrate can be varied for the specific method of screening, orienting and varying each axis as required for the given application and limitations of equipment.

EXAMPLES

To exemplify the results achieved using the methods and catalysts described in the present invention, the following examples are provided. The examples are intended to illustrate, but not to limit, the scope of the invention. All parts are by weight unless otherwise indicated.

Example 1

The following is an example of a screening procedure to determine the optimum catalyst for synthesis of an optically enriched cyanoamine. A spatially addressed library of tripeptides was synthesized on Wang resin (0.7 mmol/g loading) consisting of the following components: glycine, via a carboxy linkage was coupled to the resin. This was then distributed into 625 wells in a 25×25 grid. Rows 1–25 were reacted under standard peptide coupling methods (EDC, HOBt, t-BOC-$AA_1$, $CH_2Cl_2$) with the corresponding amino acids in Column A. Deprotection ($CF_3COOH$, $CH_2Cl_2$) of the amines was followed by coupling columns 1–25 with the corresponding amino acids (EDC, HOBt, t-BOC-$AA_2$, $CH_2Cl_2$) from column B:

|     | Column A | Column B |
| --- | --- | --- |
| 1.  | tert-Leucine | (Acm) Cysteine |
| 2.  | Leucine | Norleucine |
| 3.  | Isoleucine | Cyclohexylalanine |
| 4.  | Valine | Phenylglycine |
| 5.  | Alanine | Methionine |
| 6.  | Glycine | D-Phenylalanine |
| 7.  | Phenylalanine | (Trt) Histidine |
| 8.  | (O-tert-Butyl) Threonine | HPh |
| 9.  | Cyclohexylglycine | Proline |
| 10. | (O-tert-Butyl) Serine | (Tosyl) Arginine |
| 11. | (Trityl)Asparagine | (O-tert-Butyl) Tyrosine |
| 12. | (Trityl) Glutamine | (O-tert-Buytl) Glutamic Acid |
| 13. | (O-tert-Buytl) Aspartic acid | (O-tert-Buytl) Aspartic Acid |
| 14. | (O-tert-Buytl) Glutamic acid | (Trityl) Glutamine |
| 15. | (O-tert-Butyl) Tyrosine | (Trityl) Asparigine |
| 16. | (Tosyl) Arginine | (O-tert-Butyl) Serine |
| 17. | Proline | Cyclohexylglycine |
| 18. | Hph | (O-tert-Butyl) Threonine |
| 19. | (Trt) Histidine | Phenylalanine |
| 20. | (O-Benzyl) Serine | Glycine |
| 21. | Methionine | Alanine |
| 22. | Phenylglycine | Valine |
| 23. | Cyclohexylalanine | Isoleucine |
| 24. | Norleucine | Leucine |
| 25. | (Trityl) Threonine | tert-Leucine |

The aliquots of this set of compounds were in turn treated in 25 separate experiments with the following 25 aldehydes (1.0 equiv of aldehyde/1.0 equiv tripeptide, toluene, azeotrope×5):

| | |
| --- | --- |
| 3,5-Dichlorosalicylaldehyde | 5-Bromosalicylaldehyde |
| 3-Methoxy-5-nitrosalicylaldehyde | 4-Hydroxybenzaldehyde |
| 4-Hydroxysalicylaldehyde | 3-Hydroxybenzaldehyde |
| 5-Bromo-3-nitrosalicylaldehyde | 3,5-Dinitrosalicylaldehyde |
| 4-Diethylaminosalicylaldehyde | 5-Hydroxysalicylaldehyde |
| 3-Hydroxysalicylaldehyde | 3,5-Diiodosalicylaldehyde |
| 4-Bromo-3-methoxysalicylaldehyde | 4,6-Dimethoxy-salicylaldehyde |

-continued

| | |
|---|---|
| 5-Methoxysalicylaldehyde | Furfural |
| 3-Hydroxy-2-naphthylaldehyde | 4,6-Dihydroxysalicylaldehyde |
| 3,5,6-Trichlorosalicylaldehyde | Salicylaldehyde |
| 2-Hydroxy-1-naphthylaldehyde | 3-Methoxysalicylaldehyde |
| 4-Methoxysalicylaldehyde | 3,5-Dibromosalicylaldehyde |
| 5-Nitrosalicylaldehyde | |

This provided 15625 spatially addressed tripeptide Schiff base compounds. The ligands were transferred into a glovebox, and each ligand was treated with titanium tetraisopropoxide (100 ul of a 0.7M solution in toluene). Pivaloyl-benzhydrylimine was added (100 ul of a 0.7M solution in toluene), followed by trimethylsilyl cyanide (100 ul of a 1.4M solution in toluene. The mixtures were covered, then shaken at room temperature for 16 hours. The reactions were removed from the glovebox, ether (200 ul, sat'd w/H$_2$O) was added, and the plates were filtered using silica-prepacked PKP filter plates and a UNI-VAC manifold (Polyfiltronics products). Collection in 96-well 2-ml microtiter plates, and subsequent chiral HPLC analysis indicated that the preferred ligand for this transformation consisted of Salicylaldehyde-tert-Leucine-(O-tert-Butyl)Threonine-Glycine.

Example 2

The following is an example of a solution phase catalyzed reaction to synthesize 2-chlorophenyl glycine. Screening of the above library determined that a preferred catalyst for the formation of N-(2-chloro-a-cyanobenzyl)benzhydrylamine was 3,5-Dichlorosalicylaldehyde-tert-Leucine-(O-tert-Butyl)Threonine-Glycine. 3,5-Dichlorosalicylaldehyde-tert-Leucine-(O-tert-Butyl)Threonine-Glycine methyl ester was synthesized using standard solid-phase synthesis techniques and was added (53.3 mg, 0.1 mmol) under a nitrogen atmosphere to a solution of titanium tetraisopropoxide (29.5 ul, 0.1 mmol) in toluene (2 ml), and the mixture was stirred for about 15 minutes. Ortho-chlorobenzylidenylbenzhydrylamine (306 mg, 1.0 mmol) was added and the mixture stirred until complete dissolution of the substrate (ca. 10 minutes). Trimethylsilylcyanide (267 ul, 2.0 mmol) was added to the solution and the resultant mixture was stirred for 48 hours. Addition of ether (2 ml, 5% water) followed by filtration through silica afforded a product that was predominantly the desired isomer contaminated with a small amount of starting material. Addition of hexanes to the ethereal solution afforded pure N-(2-chloro-a-cyanobenzyl)benzhydrylamine as white crystals. Analysis by HPLC indicated optical purity of >99%.

The above product was dissolved in aqueous hydrochloric acid (6N, 10 ml) and heated at 70° C. for six hours (until exhaustion of the nitrile). The reaction mixture was cooled to room temperature, made basic (pH >10) by addition of solid potassium carbonate, then with aqueous potassium hydroxide (2M, ca. 5 ml). Washing with ether (3×30 mL), followed by titration to pH 6.5 and concentration of the aqueous phase afforded, upon cooling, a white solid, which was recrystallized to afford a near quantitative yield of L-2-chlorophenylglycine. Analysis by HPLC indicated optical purity of >99%.

Example 3

Salicylaldehyde-tert-Leucine-(O-tert-Butyl)Threonine-Glycine (5 uL of a 0.7M solution) was treated with titanium tetraisopropoxide (100 ul of a 0.7M solution in toluene). Pivaloyl-benzhydrylimine was added (100 uL of a 0.7M solution in toluene), followed by trimethylsilyl cyanide (100 ul of a 1.4M solution in toluene). The mixture was stirred as one molar equivalent of isopropanol in toluene was added in small increments over 24 hours. Ether (200 ul, sat'd w/H$_2$O) was added, and the reaction was through silica (400–230 mesh). Subsequent chiral HPLC analysis indicated complete consumption of the starting imine and chirally enriched cyanoamine. Hydrolysis of the product in 6M aqueous HCl afforded, after recrystallization, optically pure S-tert-leucine.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:
1. A chemical compound comprising the formula:

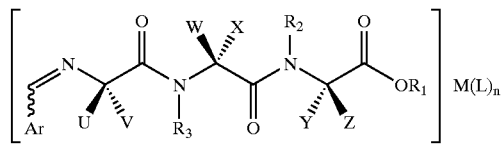

wherein

U, V, W, X, Y, and Z are each, independently, selected from the group consisting of hydrogen, aryl, aralkyl, alkaryl, and heterocyclic group;

Ar is a substituted or unsubstituted 2-hydroxyaryl group;

$R_1$ is alkyl, aryl, or heterocyclyl;

$R_2$ and $R_3$ are each independently hydrogen;

M is a metal ion;

L is a counterion; and n is an integer.

2. A compound of claim 1, wherein V and W are hydrogen.

3. A compound of claim 1, wherein U and X are hydrogen.

4. A compound of claim 1, wherein M is titanium.

5. A compound of claim 1, wherein L is 2-propoxide.

* * * * *